(12) United States Patent
Messina

(10) Patent No.: US 6,254,880 B1
(45) Date of Patent: Jul. 3, 2001

(54) DEER REPELLENT AND METHOD

(76) Inventor: James Messina, 58 Califon Rd., Long Valley, NJ (US) 07853

( * ) Notice: Subject to any disclaimer, the term of this patent is extended or adjusted under 35 U.S.C. 154(b) by 0 days.

(21) Appl. No.: 09/324,535

(22) Filed: Jun. 2, 1999

(51) Int. Cl.$^7$ .................................................. A01N 25/32

(52) U.S. Cl. .................... 424/407; 424/405; 424/406; 424/409; 424/421; 514/920

(58) Field of Search .................... 514/920; 424/405–407, 424/409–411, 413, 421, 485, 529, 581, 195.1, 418; 426/647

(56) References Cited

U.S. PATENT DOCUMENTS

| 5,368,866 | * | 11/1994 | Loucas | 424/581 |
| 5,783,204 | * | 7/1998 | Messina | 424/406 |

* cited by examiner

Primary Examiner—Neil S. Levy
(74) Attorney, Agent, or Firm—Graham, Curtin & Sheridan; Richard T. Laughlin, Esq.

(57) ABSTRACT

A deer repellent formulation and method for warding off a deer from a shrub or plant. The formulation is an admixture of water, eggs, adhesive and animal blood. Hot peppers can also be added to the formula. The formulation can be applied to a support medium such as clay or a length of rope and then associated with the vegetation to be protected.

5 Claims, No Drawings

DEER REPELLENT AND METHOD

FIELD OF THE INVENTION

The invention generally relates to a deer repellent, and in particular the invention relates to a deer repellent composition which can be applied to a wide range of surfaces and to a method for the use of such a composition.

BACKGROUND OF THE INVENTION

The prior art deer repellent formulation is described in U.S. Pat. No. 4,965,070, issued Oct. 23, 1990 to the same inventor as this application. The prior art formulation consisted essentially of by volume: 68 to 90% water; 6 to 10% thiram; 0.5 to 2% chicken eggs; 1 to 2% liquid hot sauce; 2 to 16% adhesive to aid in adhering to vegetation and 0.5 to 2% coloring dye.

One problem of the prior art deer repellent formulation is that although the ingredients are common materials it requires approval of the EPA which involves long and costly tests. The formulations of this type are applied by small companies such as landscape gardeners, and the obtaining of approval from the EPA is financially prohibitive. This results in widespread destruction of homeowners landscaping because of the unfettered proliferation of deer in suburban areas. Further, the prior art materials have a limited effective life as well as the odor of the formulation can limit its acceptance.

OBJECTS OF THE INVENTION

One object of the present invention is to provide an improved deer repellent formulation for application to a shrub, or plant or the like which can be acceptable under the laws of the U.S. Environmental Protection Agency ("EPA").

Another object of the invention is to provide a deer repellent formulation more acceptable to humans.

Another object of the invention is to make use of EPA-approved components without reduction of the effectiveness of the treatment.

Other objects and the advantages of the invention will appear from the following description.

SUMMARY OF THE INVENTION

According to the present invention, a non-toxic deer repellent formulation and method for its use are provided. The formulation is an aqueous solution or mixture consisted essentially of water and a composition comprising 2 to 10% chicken egg yolks; 10 to 30% adhesive or sticker to aid in adhering to vegetation, 20 to 40% animal blood and 5 to 10% green coloring dye. Thickener can be added to give the composition the desired application characteristics. Typical would be 1 to 5% of the total composition of thickener. In addition, about 10 to about 20% of hot pepper can be added to the mixture. All of the percentages are by volume of the composition. The animal blood is preferably beef blood. This formulation has proven effective and is acceptable to the EPA.

The composition is supplied to the job site as a concentrate and the desired amount of water is added at the job site. The mixture is then applied with a power sprayer to the vegetation. As an alternate procedure, the composition can be impregnated into a rope with the rope being placed around the vegetation to be protected.

DESCRIPTION OF THE PREFERRED EMBODIMENT

The preferred deer repellent formulation is three large fresh chicken egg yolks, 1 ounce of green coloring dye, 4 ounces of animal blood, 3 ounces of adhesive to aid in adhering to vegetation or the carrier material, and about 1 teaspoon of thickener. Water is added to make a total volume of about one gallon of the aqueous mixture. A range of ingredients can be utilized such as 0.5 to 2% fresh egg yolks; 0.5 to 2% coloring dye; 2 to 16% animal blood; and 2 to 16% adhesive. In addition, about 1 to 8% hot pepper can be added. The hot pepper can be, for example, GOYA or LOUISIANA HOT.

The mixture is formed by adding the egg yolks to the water. The egg yolks act as a deterrent agent. A green coloring dye is an optional addition to the solution for blending the composition with the color of the foliage and resembles the landscape. A coloring dye, such as that sold in under the name Greenzit, can be used. The adhesive, such as that sold under the trademark "Nu-Film-P," CLEARSPRAY or the like, can be used. In particular, the adhesive is used for a deer repellent assembly, which is exposed to rain or snow.

The composition of the invention can be utilized in the manner described in U.S. Pat. No. 5,183,661 issued on Feb. 2, 1993 to James Messina. The formulation of the invention can be applied to a support medium such as a solid braid, number 8, cotton and polyester, one-quarter inch diameter, sash cord rope of 100 foot length, which is sold by the Lehigh Group, Allentown, Pa. 18105, United States. The support medium can also be a clay material, which ranges in size of clay granules or particles, from dustless fine granules to about one-quarter inch overall diameter or thickness granules. The clay material comes packaged in a 0.20 pound bag, which is made of a finely woven cloth material and which has a drawstring along an open top edge thereof, and which has a size of about 4 inches in height by about 3 inches in width when flat. The drawstring threads through spaced holes located about one-half inch down from the bag top edge.

The deer repellent assembly of support rope and formulation can be wrapped around a shrub or plant or strung between shrubs and plants. The deer repellent assembly of support medium clay material and formulation can be distributed under and around shrubs and plants, or the like.

It is noted that 16 fluid ounces of deer repellent formulation is sufficient to wet the 100 foot length of one-quarter inch diameter rope. Also, eleven fluid ounces of deer repellent formulation is sufficient to wet throughout the one pound of clay granules. A shorter rope length requires proportionally less fluid ounces of formulation based upon rope length and rope cross section areas. Less than one pound of clay granules medium requires proportionally less fluid ounces of formulation based upon medium volume.

EXAMPLE 1

The deer repellent formulation in the preferred embodiment for outdoor application as follows:

3 large chicken egg yolks of food quality 1 oz. GREENZIT (green coloring dye in an amount to produce the desired color)

5 oz. NU-FILM P (adhesive in a quantity sufficient to adhere to the plant)

1 oz. CLEARSPRAY (water base sticker)

1 tsp. thickener (control viscosity)

4 oz. beef animal blood

Water is added to make one gallon of mixture.

EXAMPLE 2

The deer repellent formulation of Example 1 can have added 2 oz. hot peppers (GOYA).

EXAMPLE 3

The deer repellent formulation concentrate is prepared having the following formulation:

5 oz. NU-FILM P
2.5 oz. GREENZIT
2.5 oz. CLEARSPRAY
1 tsp. thickener
7.5 large egg yolks of food quality
10 oz. animal beef blood of food quality Water is added to the mixture to make one quart. On site the concentrate is mixed in the ratio of 1 part concentrate to 9 parts water.

EXAMPLE 4

The deer repellent formulation concentrate is prepared having the following formulation:

5 oz. NU-FILM P
2 oz. GREENZIT
2 oz. CLEARSPRAY
1 tsp. thickener
6.0 large egg yolks of food quality
12 oz. animal beef blood of food quality Water is added to the mixture to make one quart. On site the concentrate is mixed with in the ratio of 1 one part concentrate to 9 parts water.

EXAMPLE 5

The deer repellent composition of Example 1 is utilized as follows:

100-foot length of support rope, one-quarter inch in diameter, of cotton and polyester, solid braid material.

16 fl. oz. of the deer repellent formulation as described in Example 1. The deer repellent formulation is placed in a container. The deer repellent formulation is distributed evenly along the support rope length by dipping the rope into the container.

EXAMPLE 6

The deer repellent assembly in the second embodiment is shown below:

1 lb. by weight clay granules in a particle size distribution from dustless fine particles to about one-quarter inch overall thickness particles for a support medium;

11 fl. oz. deer repellent formulation as described in Example 4. The deer repellent formulation is mixed with the support medium clay granules.

While the invention has been described in its preferred embodiment, it is to be understood that the words which have been used are words of description rather than limitation and that changes may be made within the purview of the appended claims without departing from the true scope and spirit of the invention in its broader aspects.

What is claimed is:

1. In a method of repelling deer from a shrub or plant utilizing a formulation containing coloring dye for blending the appearance of the formulation with its environment and an adhesive for adhering the composition to a carrier, the improvement which comprises the steps of:

preparing a deer repellent formulation by admixing about 15 fluid ounces of water, about 0.125 ounces by weight of fresh chicken egg yolks, about 0.968 ounces by weight of beef animal blood and about 2 to 16% by weight of the adhesive;

forming a support medium for the formulation;

distributing the formulation evenly on the support medium; and disposing the support medium with the formulation on and about the shrub or plant.

2. The method of claim 1, wherein the support medium is a braided rope of about one-quarter inch diameter.

3. The method of claim 2, wherein the support medium is a volume of clay granules having a particle size distribution from dustless fine particles to about one-quarter inch thickness particles.

4. The method of claim 3, wherein the formulation measures about 16 fluid ounces per 100 foot of rope length containing per 16 fluid ounces:

fresh chicken egg yolks at about 0.125 ounces by weight;

beef animal blood at about 0.968 ounces by weight; and water at about 15 fluid ounces prior to evaporation thereof.

5. In a method of repelling deer from a shrub or plant utilizing a formulation containing coloring dye for blending the appearance of the formulation with its environment and an adhesive for adhering the composition to a carrier, the improvement which comprises the steps of:

preparing a deer repellent formulation by admixing about 15 fluid ounces of water, about 0.5 to 2% by weight of fresh chicken egg yolks and about 2 to 16% ounces by weight of beef animal blood, 0.5 to 2% of the coloring dye and 2 to 19% of the adhesive;

forming a support medium for the formulation;

distributing the formulation evenly on the support medium; and disposing the support medium with the formulation on and about the shrub or plant.

* * * * *